US005952531A

United States Patent [19]

Priestley et al.

[11] Patent Number: 5,952,531

[45] Date of Patent: Sep. 14, 1999

[54] NITRATION PROCESS

[75] Inventors: Ian Jeffrey Grassham Priestley, Blackley; James Peter Muxworthy, Huddersfield; John Heathcote Atherton, Huddersfield; Martin Lennon, Huddersfield; Stephen Martin Brown, Huddersfield, all of United Kingdom

[73] Assignee: Zeneca Limited, London, United Kingdom

[21] Appl. No.: 08/960,924

[22] Filed: Oct. 30, 1997

[30] Foreign Application Priority Data

| | | | |
|---|---|---|---|
| Nov. 1, 1996 | [GB] | United Kingdom | 9622784 |
| Jul. 28, 1997 | [GB] | United Kingdom | 9715846 |

[51] Int. Cl.[6] .......................... C07C 43/00; C07C 205/00; C07C 29/00

[52] U.S. Cl. .......................... 568/585; 568/939; 568/840; 568/424; 568/306; 560/21; 562/434; 562/435; 562/438

[58] Field of Search .................................... 568/939, 585, 568/840, 424, 306; 360/21; 562/434, 435, 438

[56] References Cited

U.S. PATENT DOCUMENTS

| | | | |
|---|---|---|---|
| 2,435,314 | 2/1948 | Kokatnur | 260/167 |
| 2,435,544 | 2/1948 | Kokatnur | 260/645 |
| 4,429,146 | 1/1984 | Liu | 560/21 |
| 4,723,985 | 2/1988 | Forster et al. | 504/196 |

FOREIGN PATENT DOCUMENTS

| | | |
|---|---|---|
| 0003416 | 6/1979 | European Pat. Off. . |
| 0 668 260 | 8/1995 | European Pat. Off. . |
| 97/10199 | 3/1997 | WIPO . |

OTHER PUBLICATIONS

Bisagni et al., Tetrahedron, 1996, vol. 52, No. 31, pp. 10427–10440, "A convenient way to dibenzo [c,h]–1, 5–naphthyridines (11–aza–benzo[c] phenanthridines)".

Masci, Tetrahedron, 1989, vol. 45(a), 2719–2730, "The Selectivity of Electrophilic Aromatic Nitration and the Effect of the Organic Solvents".

*Primary Examiner*—Paul J. Killos
*Assistant Examiner*—Jafar Parsa

[57] ABSTRACT

A process for the nitration of an aromatic or heteroaromatic compound with a nitrating agent comprising nitric acid or a mixture of nitric and sulphuric acids, characterised in that nitration is performed in a solvent comprising at least 50% v/v of a $C_1$–$C_6$ alkyl ester of a $C_1$–$C_4$ carboxylic acid. The process is of particular use for the nitration of diphenyl ethers to give compounds which are useful as herbicides or as intermediates in the synthesis of herbicides.

16 Claims, No Drawings

NITRATION PROCESS

The present invention relates to a process for nitration and, in particular, to a process for the nitration of aromatic and heteroaromatic compounds. The process is of particular use for nitrating diphenyl ethers to give compounds which are useful as herbicides or as intermediates in the synthesis of herbicides.

Various processes are known for the nitration of aromatic and heteroaromatic compounds. The most commonly used system employs sulphuric acid as the solvent or fluidising agent, and nitric acid or an alkali metal nitrate as the nitrating agent. Although effective in many cases, large quantities of waste sulphuric acid are often generated and recovery or disposal of this acid poses environmental problems. The use of an organic solvent can result in reduced disposal problems and, in some cases, improved yields. Chlorinated solvents have been described as suitable for this purpose, for example, EP-A-0022610, which relates to herbicides of the formula:

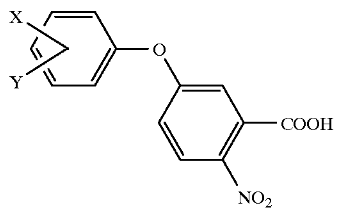

wherein X and Y may be H, F, Cl, Br, $CF_3$, $OCF_2CHZ_2$ (Z=Cl, Br, F), $OCH_3$, CN, $CO_2R$ (R=lower alkyl), $C_6H_5$, O-alkyl, $NO_2$ or $SO_2$-lower alkyl;

describes a process for making these compounds by nitrating a compound of the formula:

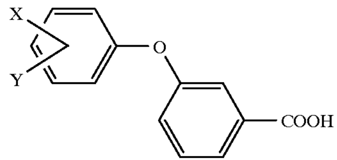

wherein X and Y are as defined above. Suggested nitrating agents for this reaction include mixtures of nitric and sulphuric acids and the recommended reaction solvent is dichloromethane. The nitration process is said to give a yield of 75.4% but no details are given of the purity of the product or the presence of other nitrated isomers.

U.S. Pat. No. 4,031,131 describes similar compounds to the above which are prepared in a similar manner. Suggested nitrating agents include potassium nitrate or mixed nitric and sulphuric acids and the reaction is carried out in dichloromethane. An extremely high yield (>95%) is claimed for the nitration reaction but, again, there are no details given about the purity of the product. Nitration reactions using mixed nitric and sulphuric acids may also be carried out in the presence of acetic anhydride.

EP-A-0003416 and EP-A-0274194 both relate to the synthesis of herbicidal compounds of the formula:

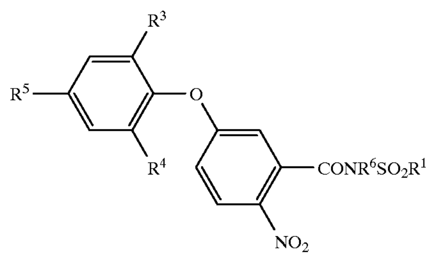

wherein $R^1$ is alkyl optionally substituted with fluorine or optionally substituted phenyl;

$R^3$ is H, F, Cl, Br, I, alkyl, trifluoromethyl or CN;

$R^4$ is H, F, Cl, Br, I or trifluoromethyl;

$R^5$ is F, Cl, Br, I or trifluoromethyl; and $R^6$ is H or $C_1$–$C_4$ alkyl.

In EP-A-0003416, these compounds may be obtained by nitrating the corresponding carboxylic acid or carboxamide and then converting to the sulphonamide, or by nitrating the sulphonamide itself. A nitration reaction is described in Example 7 where the solvent is 1,2-dichloroethane and the nitrating agent is a mixture of potassium nitrate and concentrated sulphuric acid.

EP-A-0274194 describes a process for the nitration of compounds of the formula:

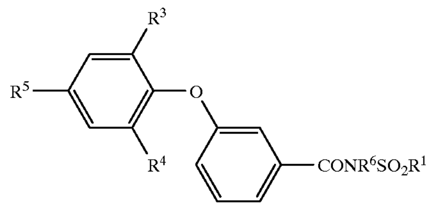

The nitration reaction is carried out using a nitrating agent such as concentrated nitric acid or sodium nitrate, or mixtures of these with sulphuric acid. The reaction solvent is one which is resistant to nitration, examples of such solvents include halogenated solvents such as dichloromethane, dichloroethane, dichloropropane, chlorofluorocarbons and aromatic solvents such as nitrobenzene.

However, none of the above mentioned methods are particularly satisfactory for use on an industrial scale because they all have the common problem that the reaction yields a mixture of the required product and other nitrated isomers. Nitrated isomers of diphenyl ether compounds are often extremely difficult to separate from one another and the quantity of other isomers is often too high for the final product to fulfil the requirements of the regulatory authorities for herbicides. The problem tends to be further exacerbated if the nitrated product is an intermediate in the synthesis of a herbicide rather than the required herbicide itself, because the mixture of nitrated compounds means that larger quantities of other reagents must be used than would be necessary if the nitrated isomers could be separated satisfactorily. It is therefore important to ensure that the nitration process produces a product mixture containing the highest possible proportion of the desired isomer.

The problem of obtaining mixtures of isomers from such a nitration process was recognised in GB-A-2103214 which describes a process in which a compound of the formula:

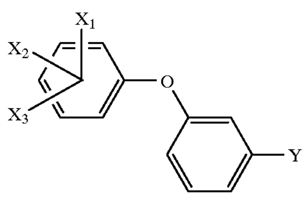

wherein each of $X_1$, $X_2$ and $X_3$ is H, F, Cl, Br, $CF_3$, $OCF_2CHZ_2$ (where Z is F, Cl or Br), $OCF_3$, CN, $CO_2R$ (R is lower alkyl), phenyl, lower alkoxy, $NO_2$ or $SO_2R$ (R is lower alkyl), and at least one of $X_1$, $X_2$ and $X_3$ is other than H; and Y is $CO_2R$ (R is lower alkyl) or carboxy;

is nitrated to give a product of the formula:

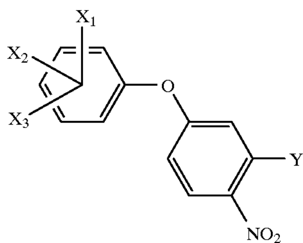

wherein $X_1$, $X_2$, $X_3$ and Y are as defined above.

The nitration is carried out using a mixture of nitric and sulphuric acids in an organic solvent such as dichloromethane. The desirability of keeping the reaction system anhydrous by the addition of acetic anhydride is stressed, GB-A-2103214 states that this makes it possible to improve the selectivity with respect to acifluorfen (the desired nitrated product). The recommended ratio of starting material:solvent:acetic anhydride is 1:2.66:1.4. The reaction is conducted at a temperature of 45° C. and left for 3 hours. The reaction mixture is then allowed to stand so that the organic and aqueous phases separate and the organic solvent removed by distillation. PCT/GB96/01892 relates to a similar process in which the preferred solvent is again a halogenated solvent, namely tetrachloroethylene (TCE).

The prior art nitration processes described above are thus generally conducted in halogenated solvents. Whilst these are useful solvents in many respects, they do have disadvantages, one of the most serious being that they present a threat to the environment if they are released. Processes which lead to environmental damage are becoming less and less acceptable and it would therefore be of great benefit if alternative solvents could be found, however, despite their potential environmental benefits, non-chlorinated solvents have rarely been used in industrial nitrations.

Schofield, "Aromatic Nitration", Cambridge University Press, 1981, describes the use of acetic acid, nitromethane, sulpholane, acetonitrile and ethers as nitration solvents. U.S. Pat. No. 4,306,900 discloses acetic acid as a solvent for the nitration of diphenyl ethers. However, in all of these cases, the solvents are difficult to handle and are water miscible making recovery and reuse problematic.

*Tetrahedron*, 1989, 45(9), 2719–2730, describes an investigation into the selectivity of aromatic nitrations using $Bu_4NNO_3$ and $(CF_3CO)_2O$ in a variety of organic solvents including ethyl acetate and halogenated solvents such as dichloromethane.

*Tetrahedron*, 1996, 52(31), 10427–10440, describes the nitration of 3-phenylisoquinoline-1-(2H)-ones using nitric acid in acetic acid containing about 20% v/v ethyl acetate, to give 3-phenyl-4-nitro-isoquinoline-1-(2H)-ones and traces of other uncharacterised nitrated derivatives.

The present invention provides a process for the nitration of an aromatic or heteroaromatic compound with a nitrating agent comprising nitric acid or a mixture of nitric and sulphuric acids, characterised in that nitration is performed in a solvent comprising at least 50% v/v of a $C_1$–$C_6$ alkyl ester of a $C_1$–$C_4$ carboxylic acid.

In the process of the invention it is an aromatic ring carbon of the aromatic or heteroaromatic compound which is nitrated. The aromatic or heteroaromatic compound is preferably selectively mono-nitrated using the process of the invention.

The esters used as solvents in the process of the present application are non-toxic, readily recoverable and do not present a threat to the environment in the event of an accidental release. It would have been expected that in order to obtain the environmental benefit of using a non-halogenated solvent, the efficiency of the process would suffer in some way. However, this has, surprisingly, been found not to be the case when the nitration is performed in a solvent comprising at least 50% v/v of a $C_1$–$C_6$ alkyl ester of a $C_1$–$C_4$ carboxylic acid.

In the context of the present invention the term "aromatic compound" refers to a compound comprising an aromatic ring system which may be mono-, bi- or tricyclic. Examples of such ring systems include phenyl, naphthalenyl, anthracenyl and phenanthrenyl.

The term "heteroaromatic compound" refers a compound comprising an aromatic ring system containing at least one heteroatom which may be mono-, bi- or tricyclic. Preferably, single rings will contain up to four, and bicyclic systems up to five heteroatoms, these are preferably chosen from nitrogen, oxygen and sulphur. Nitrogen atoms in the ring may be quatemised or oxidised. Examples of such ring systems include furyl, thienyl, pyrrolyl, pyrazolyl, imidazolyl, 1,2,3-triazolyl, 1,2,4-triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, 1,2,3,4-oxatriazolyl, 1,2,3,5-oxatriazolyl, 1,2,3,4-thiatriazolyl, 1,2,3,5-thiatriazolyl, pyridyl, pyrimidinyl, pyridazinyl, pyrazinyl, 1,2,3-triazinyl, 1,2,4-triazinyl, 1,3,5-triazinyl, 1,2,4,5-tetrazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl.

The aromatic or heteroaromatic compound to be nitrated according to the process of the invention may optionally be substituted with one or more substituents. Examples of substituents include $C_1$–$C_6$ alkyl, $C_2$–$C_6$ alkenyl or $C_2$–$C_6$ alkynyl any of which may optionally be substituted with one or more substituents selected from, for example, halogen and hydroxy; halo e.g. fluoro, chloro, bromo or iodo; $C_1$–$C_6$ alkoxy optionally substituted by halogen e.g. methoxy, ethoxy, n-propoxy, iso-propoxy, difluoromethoxy, trifluoromethoxy or tetrafluoroethoxy; aryl e.g. optionally substituted phenyl; aryloxy e.g. optionally substituted phenyloxy; cyano; nitro; amino; mono- or di-$C_1$–$C_6$ alkylamino; hydroxylamino; acyl e.g. acetyl or trifluoroacetyl; $S(O)_n$ $C_1$–$C_6$ alkyl or $S(O)_n$ $C_1$–$C_6$ haloalkyl, wherein n is 0, 1 or 2, e.g. methylthio, methylsulphinyl, methylsulphonyl, trifluoromethylthio trifluoromethylsulphinyl or trifluoromethylsulphonyl; SCN; $SF_5$; $COOR^4$; $COR^6$; $CONR^4R^5$ or $CONHSO_2R^4$; wherein $R^4$ and $R^5$ are each independently hydrogen or $C_1$–$C_6$ alkyl optionally substituted with one or more halogen atoms and $R^6$ is a halogen atom or a group $R^4$.

When there is more than one substituent, the substituents may be the same or different.

The aromatic or heteroaromatic compound to be nitrated according to the process of the invention preferably comprises a substituted phenyl ring.

More preferably the aromatic or heteroaromatic compound to be nitrated according to the process of the invention comprises a diphenyl ether the phenyl rings of which are independently optionally substituted by one or more groups selected from $C_1$–$C_6$ alkyl, $C_2$–$C_6$ alkenyl or $C_2$–$C_6$ alkynyl any of which may optionally be substituted with one or more substituents selected from halogen and hydroxy; halo; $COOR^4$; $COR^6$; $CONR^4R^5$ or $CONHSO_2R^4$; wherein $R^4$ and $R^5$ are each independently hydrogen or $C_1$–$C_6$ alkyl optionally substituted with one or more halogen atoms and $R^6$ is a halogen atom or a group $R^4$.

The process according to the present in invention is of particular use for the nitration of diphenyl ether compounds which are useful as herbicides or as intermediates in the synthesis of herbicides.

Therefore, according to a further aspect of the present invention, there is provided a process for the preparation of a compound of formula I:

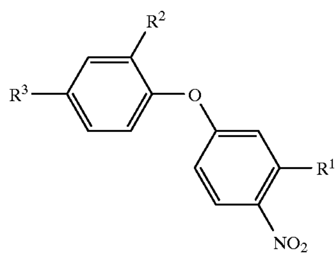

wherein $R^1$ is hydrogen or $C_1$–$C_6$ alkyl, $C_2$–$C_6$ alkenyl or $C_2$–$C_6$ alkynyl (any of which may optionally be substituted with one or more substituents selected from halogen and hydroxy) or $COOR^4$, $COR^6$, $CONR^4R^5$ or $CONHSO_2R^4$;

$R^2$ is hydrogen or halo;

$R^3$ is $C_1$–$C_4$ alkyl, $C_2$–$C_4$ alkenyl or $C_2$–$C_4$ alkynyl (any of which may optionally be substituted with one or more halogen atoms) or halo;

$R^4$ and $R^5$ independently represent hydrogen or $C_1$–$C_4$ alkyl optionally substituted with one or more halogen atoms; and $R^6$ is a halogen atom or a group $R^4$;

the process comprising reacting a compound of formula II:

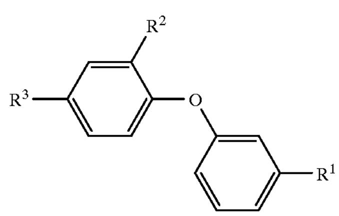

wherein $R^1$, $R^2$ and $R^3$ are as defined for formula I;

with a nitrating agent comprising nitric acid or a mixture of nitric and sulphuric acids, characterised in that nitration is performed in a solvent comprising at least 50% v/v of a $C_1$–$C_6$ alkyl ester of a $C_1$–$C_4$ carboxylic acid.

The term "$C_1$–$C_6$ alkyl" refers to a saturated straight or branched hydrocarbon chain containing from 1 to 6 carbon atoms. Examples include methyl, ethyl, n-propyl, t-butyl, n-pentyl and n-hexyl. The term "$C_1$–$C_4$ alkyl" is a subset of $C_1$–$C_6$ alkyl and refers to an alkyl group having from 1 to 4 carbon atoms.

The term "$C_2$–$C_6$ alkenyl" refers to a straight or branched hydrocarbon chain containing from 2 to 6 carbon atoms and having at least one double bond. Examples include ethenyl, allyl, propenyl and hexenyl. The term "$C_2$–$C_4$ alkenyl" is a subset of $C_2$–$C_6$ alkenyl and refers to an alkenyl group having from 2 to 4 carbon atoms.

The term "$C_2$–$C_6$ alkynyl" refers to a straight or branched hydrocarbon chain containing from 2 to 6 carbon atoms and having at least one triple bond. Examples include ethynyl, propynyl and hexynyl. The term "$C_2$–$C_4$ alkynyl" is a subset of $C_2$–$C_6$ alkynyl and refers to an alkynyl group having from 2 to 4 carbon atoms.

The term "halogen" refers to fluorine, chlorine, bromine or iodine and the corresponding term "halo" refers to fluoro, chloro, bromo or iodo.

In the context of the present invention, compounds of general formula I are designated 4-nitro isomers. Various isomers may be generated in the nitration reaction other than the required 4-nitro isomer and these include the following mono-nitro isomers:

the 2-nitro isomer:

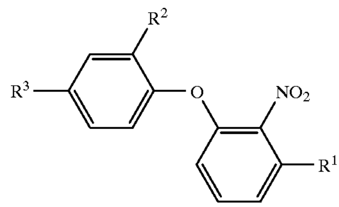

and the 6-nitro isomer:

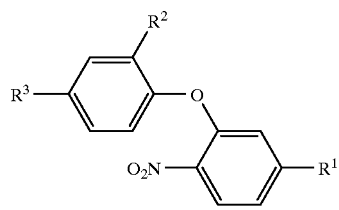

There are also at least three different dinitro isomers which may be generated.

The process of the present invention is particularly favorable as it leads to very low levels of dinitration. Indeed the proportion of dinitrated isomers is far lower than that when the reaction is conducted in TCE, which is described in PCT/GB96/01892 as a particularly favorable solvent. The levels of dinitro-isomers are also lower than with other halogenated solvents such as ethylene dichloride (EDC).

Not only are the levels of dinitrated isomers lower using the process of the present invention than with comparable processes carried out in halogenated solvents, but the proportions of the 2- and 6-nitro isomers are also considerably lower than with many halogenated solvents. In PCT/GB96/01892, TCE is the solvent of choice because its use leads to extremely low proportions of 2- and 6-nitro isomers in the product mixture. Unexpectedly, it has been found that when at least 50% v/v of a $C_1$–$C_6$ alkyl ester of a $C_1$–$C_4$ carboxylic acid is used as solvent, the levels of the 2- and 6-nitro isomers are comparable to the levels when the reaction is conducted in TCE and far lower than when the reaction is conducted in other halogenated solvents such as EDC.

Most significantly of all, the use of at least 50% v/v of a $C_1$–$C_6$ alkyl ester of a $C_1$–$C_4$ carboxylic acid as solvent enables far better solubilisation of the reactants and products than is achievable with halogenated solvents. This in turn increases the efficiency of the reaction.

The benefits of the present invention would certainly not have been predicted from the prior art as all previous similar nitrations have been conducted in halogenated solvents.

Although any $C_1$–$C_6$ alkyl ester of a $C_1$–$C_4$ carboxylic acid, or mixture thereof, can be used, shorter chain alkyl groups are preferred. Therefore, the preferred solvents for the present invention are $C_1$–$C_4$ alkyl esters, e.g. ethyl, propyl or n-butyl esters, of $C_1$–$C_4$ carboxylic acids. The reason for this is that it is necessary to use a solvent of sufficient polarity to dissolve the starting material and the product and the shorter chain esters are more polar than the longer chain ones. Similarly, esters of acetic acid and propionic acid may be more suitable than esters of butanoic acid.

Preferred solvents include ethyl acetate and n-butyl acetate, especially n-butyl acetate.

The solvent used in the process according to the invention preferably comprises at least 75% v/v of a $C_1$–$C_6$ alkyl ester of a $C_1$–$C_4$ carboxylic acid, and more preferably at least 90% v/v of a $C_1$–$C_6$ alkyl ester of a $C_1$–$C_4$ carboxylic acid.

It has also been found that there are benefits if the process of the invention is conducted in the presence of acetic anhydride. The molar ratio of acetic anhydride to starting material, e.g. compound of formula II, is preferably from about 1:1 to about 3:1.

Reaction temperature plays a role in determining the proportions of the various mono-nitrated isomers, with a greater proportion of the required isomer being produced as the reaction temperature is reduced. The reaction temperature, is thus a compromise since, clearly, it would not be economically viable to operate the reaction if the temperature were below a certain level because of the amount of cooling required. The preferred temperature range for the process of the present invention is from about −15° to about 15° C., preferably −10° to 10° C., and more preferably <0° C.

It has also been found advantageous to have a weight ratio of solvent to starting material, e.g. compound of formula II (including any isomers present), of no greater than 8.5:1, and it is preferred that the ratio is from 1.5:1 to 4:1.

As mentioned, the nitrating agent used in the process is nitric acid or a mixture of nitric and sulphuric acids. A mixture of nitric and sulphuric acids (mixed acid) may contain, for example, from about 30 to 45% of pure nitric acid, more typically from about 30 to 35% pure nitric acid.

When the chosen nitrating agent is a mixed acid, it will typically be added to the reaction mixture over a period of about 30 minutes to 15 hours. The rate of addition will, however, vary according to the reaction solvent which is chosen, with addition over about 1 to 6 hours, or preferably 2 to 4 hours, being appropriate for many solvents.

When both nitric and sulphuric acids are used in the process of the invention it is possible to further reduce the level of over nitration by adding these acids sequentially to the reaction mixture. It has been found particularly advantageous to add the sulphuric acid to a mixture of the starting material, e.g. compound of formula II, and acetic anhydride in the chosen solvent, followed by addition of the nitric acid. When a sequential addition of the sulphuric and nitric acids is used the nitric acid is preferably ≧90% strength, e.g. 90–97% strength. The use of nitric acid of ≧90% strength has the advantage that it requires a shorter reaction time than comparable reactions using e.g. 70% strength nitric acid. The molar ratio of sulphuric acid:starting material used in the reaction will generally be up to 1.5:1, however a ratio of sulphuric acid:starting material of from 0.1:1 to 0.3:1 is preferred.

When the process of the invention is used for the preparation of a compound of formula I, it is especially preferred that $R^2$ is chloro and $R^3$ is trifluoromethyl. Particularly preferred compounds of formula I are those in which $R^1$ is COOH or $CONHSO_2CH_3$. These compounds are 5-(2-chloro-α,α,α-trifluoro-4-tolyloxy)-2-nitrobenzoic acid (acifluorfen) and 5-(2-chloro-α,α,α-trifluoro-4-tolyloxy)-N-methanesulphonyl-2-nitrobenzamide (fomesafen), both of which are potent herbicides.

In addition to being a herbicide in its own right, acifluorfen may also serve as an intermediate in the synthesis of fomesafen. Therefore, according to a further aspect of the invention, there is provided a process as described above, wherein the compound of formula I is acifluorfen and which further comprises the steps of converting the acifluorfen to fomesafen. The acifluorfen may be converted to its acid chloride which may then be reacted with methane sulphonarnide to give fomesafen, both of these steps may be carried out by conventional methods, for example as described in EP-A-0003416.

The invention will now be illustrated by way of the following examples in which the following abbreviations are used:

$$pph - \text{parts per hundred} = \frac{\text{parts of by-product by weight} \times 100}{\text{parts of desired product}}$$

"mixed acid"—a mixture containing 33.4% nitric acid and 66.6% sulphuric acid.

The results for yield and quality are given in Table 1. The improved solution characteristics of the ester solvent system are illustrated in Table 2.

EXAMPLE 1

General Method for the Nitration of N-methanesulphonyl 3-(2-chloro-α,α,α-trifluoro-4-tolyloxy)benzamide in acetate ester solvents N-Methanesulphonyl 3-(2-chloro-α,α,α-trifluoro-4-tolyloxy)benzamide (86% strength, 10 g) was dissolved in the acetate ester solvent (Table 1). To this solution was added acetic anhydride (Table 1) and sulphuric acid (0.1 g). The reaction mass was cooled to 0–5° C. and mixed acid (7.2 g) added at this temperature over 2 hours with efficient agitation. Further small additions of the mixed acid were added as required until the ratio of product to starting material was 100:1 or less. Water (10 g) was added to the final reaction mixture and the resultant aqueous acid phase separated off. The solvent layer was washed with water (50 g), dried ($MgSO_4$) and evaporated to give N-methanesulphonyl 2-nitro-5-(2-chloro-α,α,α-trifluoro-4-tolyloxy) benzamide (Table 1).

EXAMPLE 2

General Method For Nitration of 3-(2-chloro-α,α,α-trifluoro-4-tolyloxy)benzoic acid to give 2-nitro-5-(2-chloro-α,α,α-trifluoro-4-tolyloxy)benzoic acid (acifluorfen)

3-(2-Chloro-α,α,α-trifluoro-4-tolyloxy)benzoic acid (86% strength, 10 g) was dissolved in a mixture of acetate ester solvent and acetic anhydride (Table 1) by gentle warming if necessary. Sulphuric acid (0.1 g) was added and the mixture cooled to 0–5° C. Mixed acid (6.3 g) was added at this temperature over 2 hours with efficient agitation. After a further period at 0–5° C. for completion of the reaction, a small amount of water was added and the resultant aqueous acid phase separated off. The solvent layer was washed with water (14 g), dried ($MgSO_4$) and evaporated to give 2-nitro-5-(2-chloro-α,α,α-trifluoro-4-tolyloxy) benzoic acid (Table 1).

EXAMPLE 3

Nitration of 3-(2-chloro-α,α,α-trifluoro-4-tolyloxy) benzoic acid to give 2-nitro-5-(2-chloro-α,α,α-trifluoro-4-tolyloxy)benzoic acid (acifluorfen) using split nitric/sulphuric acid addition Acetic anhydride (37.7 g) was added to 3-(2-chloro-α,α,α-trifluoro-4-tolyloxy)-benzoic acid (86% strength, 45 g) in n-butyl acetate (85.8 g) at 35° C. Sulphuric acid (98%, 12.2 g) was added slowly and the mixture cooled to 0° C. Nitric acid (90%, 10.4 g) was then added slowly over about 3 hours such that the temperature was maintained at −5 to 0° C. On completion of the nitric acid addition the reaction was quenched with water (60 g) at 0° C. The mixture was warmed to 50–60° C. and the aqueous layer removed. The solvent layer was washed with water (2×100 g) at 60° C. and the aqueous layer removed. The solvent and acetic acid were removed by distillation to give 2-nitro-5-(2-chloro-α,α,α-trifluoro-4-tolyloxy) benzoic acid (85%), 2'-nitro isomer (7.5 to 8.5 pph), total dinitro's (~0.5 pph).

Abbreviations used in tables:

Benzamide—N-methanesulphonyl 3-(2-chloro-α,α,α-trifluoro-4-tolyoxy)benzamide

Benzoic acid—3-(2-chloro-α,α,α-trifluoro-4-tolyloxy) benzoic acid

EtAc—ethyl acetate n-BuAc—n-butyl acetate

DCM—dichloromethane

EDC—1,2-dichloroethane

TCE—tetrachloroethene

TABLE 1

| Reactant | Solvent Identity | Solvent Amount (g) | Temp ° C. | Acetic Anhydride mol/mol | Yield % | Product Composition (pph) 2'-nitro | 6'-nitro | over nitration |
|---|---|---|---|---|---|---|---|---|
| Benzamide | EtAc | 65 | 0–5 | 3 | 76.1 | 8.1 | 8.0 | 1.1 |
| Benzamide | EtAc | *40 | 0 . 5 | 2 | 70.5 | 8.3 | 6.8 | 0.1 |
| Benzamide | n-BuAc | 86 | 0–5 | 3 | 75.6 | 8.2 | 8.7 | 0.4 |
| Benzamide | n-BuAc | *40 | 0–5 | 2 | 71.0 | 7.9 | 6.6 | 0.4 |
| Benzoic Acid | EtAc | 29 | 0–5 | 2 | 88.6 | 7.6 | 4.3 | 0.7 |
| Benzoic Acid | EtAc | 29 | −10 | 2 | 87.4 | 7.8 | 4.3 | 0.4 |
| Benzoic Acid | EtAc | 23.2 | 0–5 | 2 | 85.6 | 8.4 | 4.9 | 0.5 |
| Benzoic Acid | EtAc | 15.6 | 0–5 | 2 | 83.2 | 8.3 | 4.9 | 1.8 |
| Benzoic Acid | EtAc | 15.6 | −10 | 2 | 85.4 | 7.5 | 4.3 | 1.2 |
| Benzoic Acid | n-BuAc | 38.6 | 0–5 | 2 | 84.9 | 7.4 | 4.3 | 0.2 |
| Benzoic Acid | n-BuAc | 22.6 | 0–5 | 2 | 88.4 | 7.1 | 4.3 | 1.1 |
| Benzoic Acid | n-BuAc | 15.3 | 0–5 | 2 | 86.3 | 7.2 | 4.2 | 1.8 |
| Benzoic Acid | EDC | 30 | 0–5 | 1.7 | 84.0 | 9.5 | 4.8 | 2.3 |
| Benzoic Acid | TCE | 27 | 0–5 | 2 | 85.3 | 7.0 | 3.6 | 6.0 |

*additional solvent added during work-up

TABLE 2

| Reactant | Solvent Identity | Solvent Amount (g) | Temp. ° C. | Acetic Anhydride mol/mol | Physical Form of Reaction mass |
|---|---|---|---|---|---|
| Benzamide | EtAc | *40 | 0–5 | 2 | Thin mobile slurry |
| | n-BuAc | *40 | 0–5 | 2 | Thin mobile slurry |
| | DCM | 50 | 0–5 | 2 | Reactant & product both insoluble giving a slurry difficult to stir |
| | TCE | 50 | 0–5 | 2 | |
| Benzoic acid | EtAc | 15.6 | 0–5 | 2 | Homogeneous solution throughout |
| | n-BuAc | 15.6 | 0–5 | 2 | |
| | EDC | 31 | 0–5 | 1.7 | Partial deposition of product |
| | TCE | 27 | 0–5 | 2 | Product deposits as it forms |

*Additional solvent added during work-up

We claim:

1. A process for the nitration of an aromatic or heteroaromatic compound with a nitrating agent comprising nitric acid or a mixture of nitric and sulphuric acids, characterised in that the nitration is performed in a solvent comprising at least 50% v/v of a $C_1$–$C_6$ alkyl ester of a $C_1$–$C_4$ carboxylic acid.

2. A process according to claim 1, wherein the aromatic or heteroaromatic compound is a substituted phenyl ring.

3. A process according to claim 1 for the preparation of a compound of formula I:

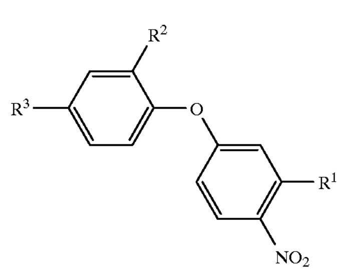

wherein $R^1$ is hydrogen or $C_1$–$C_6$ alkyl, $C_2$–$C_6$ alkenyl or $C_2$–$C_6$ alkynyl (any of which may optionally be substituted with one or more substituents selected from halogen and hydroxy) or $COOR^4$, $COR^6$, $CONR^4R^5$ or $CONHSO_2R^4$;

$R^2$ is hydrogen or halo;

$R^3$ is $C_1$–$C_4$ alkyl or $C_2$–$C_4$ alkenyl or $C_2$–$C_4$ alkynyl (any of which may optionally be substituted with one or more halogen atoms) or halo;

$R^4$ and $R^5$ independently represent hydrogen or $C_1$–$C_4$ alkyl optionally substituted with one or more halogen atoms; and $R^6$ is a halogen atom or a group $R^4$;

the process comprising reacting a compound of formula II:

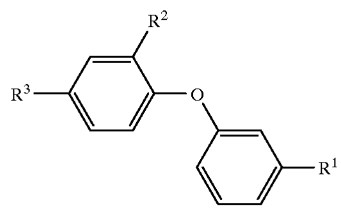

wherein $R^1$, $R^2$ and $R^3$ are as defined for formula I;

with a nitrating agent comprising nitric acid or a mixture of nitric and sulphuric acids, characterised in that the nitration is performed in a solvent comprising at least 50% v/v of a $C_1$–$C_6$ alkyl ester of a $C_1$–$C_4$ carboxylic acid.

4. A process as claimed in claim 1, wherein the solvent is an ethyl, propyl or n-butyl ester.

5. A process as claimed in claim 4, wherein the solvent is n-butyl acetate.

6. A process as claimed in claim 1, wherein the solvent comprises at least 75% v/v of a $C_1$–$C_6$ alkyl ester of a $C_1$–$C_4$ carboxylic acid.

7. A process as claimed in claim 1, wherein the nitration is conducted in the presence of acetic anhydride.

8. A process as claimed in claim 1, wherein the nitrating agent is a mixture of nitric and sulphuric acids.

9. A process according to claim 8, wherein the sulphuric and nitric acids are added sequentially to the reaction mixture.

10. A process according to claim 9, wherein the nitric acid is ≧90% strength.

11. A process according to claim 9 or 10, wherein the ratio of sulphuric acid:starting material is from 0.1:1 to 0.3:1.

12. A process as claimed in claim 1, wherein the reaction is performed at a temperature of from about −15° C. to about 15° C.

13. A process as claimed in claim 3, wherein $R^2$ is chloro and $R^3$ is trifluoromethyl.

14. A process as claimed in claim 13, wherein the compound of formula I is 5-(2-chloro-α,α,α-trifluoro-4-tolyoxy-2-nitrobenzoic acid (acifluorfen) or 5-(2-chloro-α,αα-trifluoro-4-tolyloxy)-N-methanesulphonyl-2-nitrobenzamide (fomesafen).

15. A process as claimed in claim 14, wherein the compound of formula I is acifluorfen and which further comprises the steps of converting the acifluorfen to fomesafen.

16. A process as claimed in claim 15, which comprises the steps of converting the acifluorfen to its acid chloride and treating the acid chloride with methane sulphonamide to give fomesafen.

* * * * *